United States Patent [19]

Enoch

[11] Patent Number: 4,765,732

[45] Date of Patent: Aug. 23, 1988

[54] HYPERACUITY TESTING INSTRUMENT FOR EVALUATING VISUAL FUNCTION

[75] Inventor: Jay M. Enoch, Moraga, Calif.

[73] Assignee: The Regents of the University of California, Berkeley, Calif.

[21] Appl. No.: 28,711

[22] Filed: Mar. 20, 1987

[51] Int. Cl.$^4$ ............................................... A61B 3/02
[52] U.S. Cl. ..................................... 351/243; 351/237
[58] Field of Search ............... 351/227, 230, 237, 239, 351/243, 222, 244, 225, 201, 203, 224, 226

[56] References Cited

U.S. PATENT DOCUMENTS 4,260,227  4/1981  Munnerlyn et al. ................ 351/226

OTHER PUBLICATIONS

J. M. Enoch et al., *Progress in Retinal Research*, vol. 4, Chap. 3, "Hyperacuity: A Promising Means of Evaluating Vision through Cataract", pp. 67–68, Mar. 28, 1985.

*Primary Examiner*—Rodney B. Bovernick
*Assistant Examiner*—Jay Ryan
*Attorney, Agent, or Firm*—Phillips, Moore, Lempio & Finley

[57] ABSTRACT

A hyperacuity testing instrument is adapted to evaluate visual function by selectively changing the relative position of two spots or points of light that function as visual stimuli for observation by a patient. The instrument includes a laser that emits a single beam of light that is split into two beams when it passes through a bi-prism. The beams of light are visually shown as two spots on a display screen for recorded perception by a patient. A rotary adjustment selectively varies the rotational positions of the spots relative to each other whereas a linear adjustment selectively varies the separation gap between the spots. The recorded data enables a surgeon to determine whether corrective surgery to remove an ocular media opacity will, in fact, improve vision, i.e., the test procedure "penetrates" the opacity to assess visual function at the retinal-neural level.

20 Claims, 5 Drawing Sheets

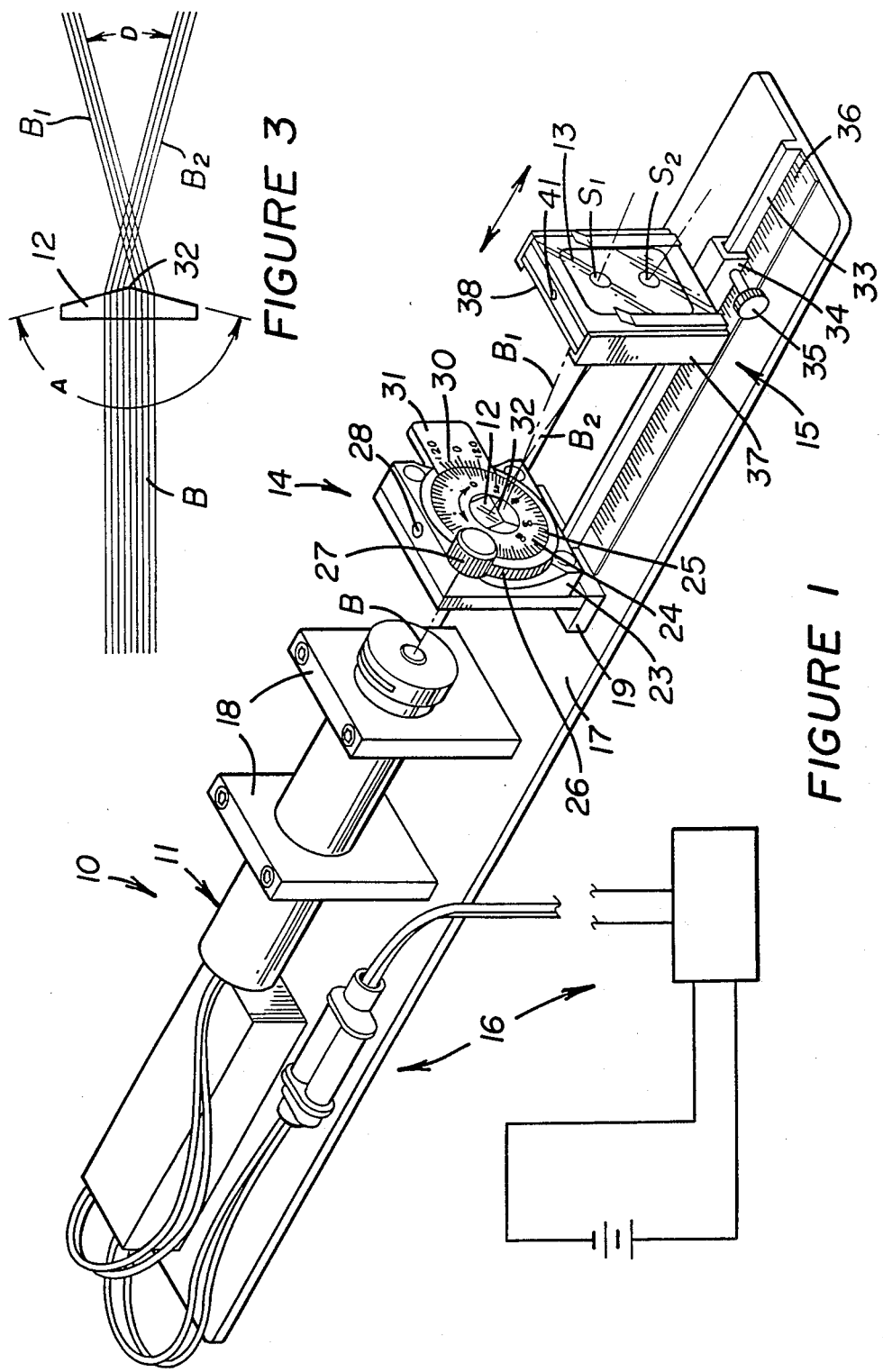

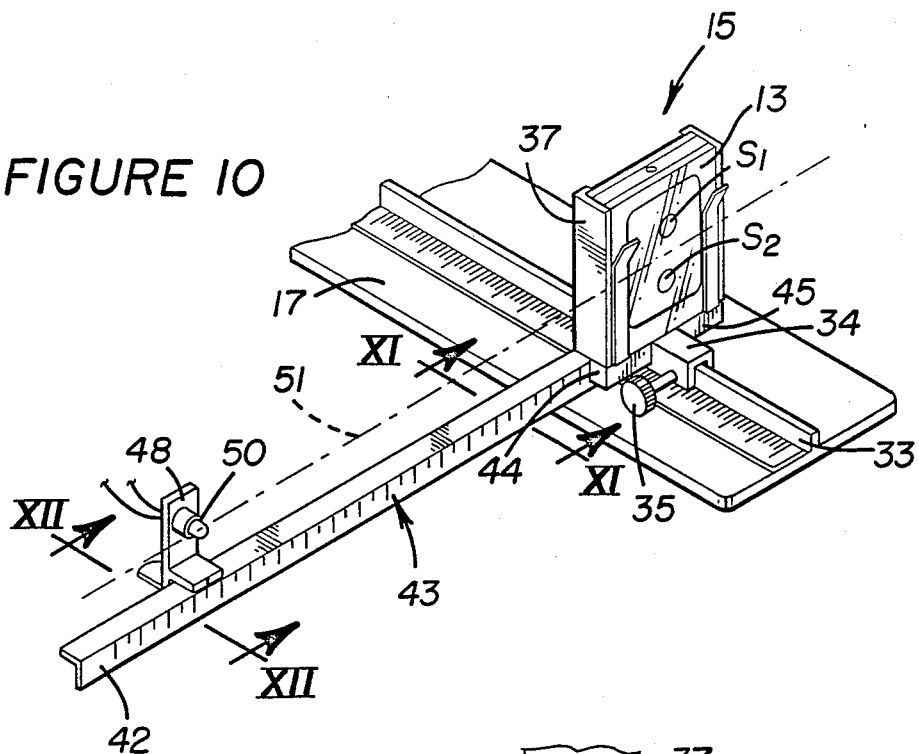
FIGURE 10
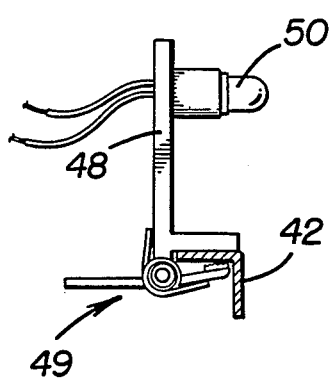
FIGURE 11
FIGURE 12

HYPERACUITY TESTING INSTRUMENT FOR EVALUATING VISUAL FUNCTION

ACKNOWLEDGMENT

This invention was made with Government support under Grant Nos. EY 03669 and EY 03674 awarded by the National Institutes of Health. The Government has certain rights in this invention.

TECHNICAL FIELD

This invention relates to a testing instrument for evaluating visual function and more particularly to an instrument for effecting hyperacuity testing of an eye to assess visual function at the retinal-neural level.

BACKGROUND ART

The development of cataracts and other opacities in the ocular media of eyes of persons is a well known. A cataract constitutes an opacity of the eye's lens that functions to scatter, disperse or absorb light and thereby obscures vision. To date, the accepted remedy for this affliction requires the surgical removal of the cataractous natural lens and compensating for its refractive power by various optical means.

This surgical technique, although normally corrective, can give rise to a degree of risk, particularly in elderly persons. The advancement of age also makes a person prone to other retinal-neural diseases and degenerative processes affecting vision, e.g., senile macular degeneration. Since a cataract obscures a clinician's view of a patient's retina and optic nerve head, as well as a patient's view of a conventional test stimulus, the detection and diagnosis of retinal disease is made correspondingly more difficult.

Prior to removing a cataract, a surgeon will seek assurance that doing so will improve the patient's vision. However, adequate assurance of this kind has proven difficult to obtain in many cases. It is thus a prevalent problem in the art and a primary object of this invention to provide a surgeon with an instrument for evaluating the functional integrity of a patient's retina and post-retinal visual pathways (retinal-neural level) before surgically removing opacities of the ocular media.

The following discussions relate to various present day instruments and test procedures for providing a surgeon with this type of pre-surgical information. Any adopted test procedure will normally recognize that several optical and physiological requirements must be satisfied to allow for adequate visual acuity. Such requirements include good retinal image quality, and intact retinal and post-retinal neural function.

A defect in the eye's optics, while resulting in poor resolution acuity, need not, however, preclude an evaluation of the neural pathways. Several commonly available test procedures are presently used clinically, but oftentimes fail when they are needed most. In particular, such test procedures tend to fail in those patients wherein the media opacity is very dense or a "window" is not present in a cataract to facilitate visual inspection of the retinal area.

One such test procedure constitutes the optical projection technique known as "potential acuity meter" (PAM). The procedure utilizes a device attached to a clinician's biomicroscope that projects a Snellen acuity chart (a standard eye chart) through a "window" or opening in an opacified eye lens. The patient simply reads the eye chart as though the patient were seeing it projected upon an external screen or wall. Unfortunately, although this technique is quite simple to use, it is only most successful in cases where the opacities are mild and will fail completely when no "window" is defined through the cataract.

Another test procedure constitutes the use of interferometry to test the visual potential of cataract patients. A laser beam or other suitable source of coherent light is split into two beams which are directed either through one or two "windows" in a cataract to produce an interference grating pattern within their overlapping retinal projection area. A patient's ability to resolve a sufficiently fine grating is interpreted as evidence of normal foveal function. Under certain conditions, however, interference acuity measurements may mislead the clinician. For example, if the grating pattern subtends a reasonably large retinal area (e.g., such as the five degree fields typical of some of these instruments), and if the stimulus is very bright (commonly the case), then visual performance of the parafoveal retina will be enhanced, and thus lead to an expectation of too good visual performance after surgery.

Thus, patients with macular dysfunction may exhibit relatively good interference grating acuity (e.g., equivalent to 20/30 to 20/60) even when their foveas are not functioning properly. In patients with macular degeneration, interference acuity may overestimate letter acuity, perhaps for this very reason. In contrast, when the required "window" or "windows" in the opacity are absent, the quality of the stimulus that is produced on the retina may be so compromised so as to preclude measurement of the patient's visual acuity, despite the presence of a healthy and normally functioning fovea.

A third test procedure constitutes electrophysiological tests wherein a patient's response to bright flashes of diffuse light [e.g., measurements of the electroretinogram (ERG) or visually-evoked cortical potential (VECP)] are recorded. This test is complicated by the fact that an ocular media opacity will function to scatter light from a "small-field" stimulus so as to cause it to fall upon a relatively large retinal area. In such cases, it may prove difficult to discriminate between responses that originate at the fovea (responsible for fine vision) and those originating in the surrounding retina. Patterned stimuli are, of course, compromised by the cataract itself and the detrimental effects of the cataract are difficult to uncouple from those which might be attributed to underlying retinal dysfunction.

The environment in which the test is performed, the type and condition of electrodes used, the amplification and filtering characteristics of the amplifier(s) (whether or not a notch filter or artifact rejection is used and, if so, the characteristics of the filter and limits of the accepted signal range), may all affect the data required for consideration and evaluation.

Tests which depend upon a subject's response to laser speckle patterns are also influenced to some degree by certain optical characteristics of the eye that are difficult to quantify in vivo. Even in those cases when the stimulus itself is exempted from consideration, valid interpretation of data obtained from these electrophysiological tests may prove difficult.

As described hereinafter, the instrument embodying this invention is particularly adapted to take advantage of a visual hyperacuity testing procedure that overcomes many of the drawbacks of the test procedures discussed above. As described in applicant's co-authored publication "Hyperacuity: A Promising Means of Evaluating Vision Through Cataract" (Progress in Retinal Research, Volume 4, Chapter 3, published by the Pergamon Press, Oxford, N.Y., on Mar. 28, 1985), the term "hyperacuity" refers to a patient's ability to successfully perform any one of a group of visual tasks, each of which requires the discrimination of very fine differences in the spatial locations of two or more visual stimuli, such as spots or points of light. While the limit of the human ability to resolve stimuli (i.e., to appreciate them as separate entities), corresponds rather well to the grain of the foveal photoreceptor matrix, the same stimuli typically need only be displaced from one another by about one-fourth this distance (or even less) for differences in their spatial positions to become apparent.

This extremely fine "hyperacuity" can be evidenced in a patients thresholds in detecting differences either in the relative positions of two lines or points (vernier acuity), in the apparent location in depth of stimuli that provides slightly different amounts of binocular image disparity (stereoacuity), or in appreciating the tilt of a single line (orientation discrimination). The robustness of the hyperacuities to variations in stimulus luminants and contrast leads to the conclusion that if a patient can reliably detect two stimuli, the patient can also compare their spatial locations with a high degree of accuracy. This characteristic of the hyperacuity test is important when considered in light of the fact that cataracts absorb, reflect, and scatter light.

Despite the fact that a cataractous eye receives an image of the external world that is more blurred, dimmer, and of lower contrast than that obtained via transplant optical media, good hyperacuity can still be expected, provided that the retina is healthy. The above publication further discusses the fact that the ability to recognize a Snellen letter (the standard eye chart method for testing vision) is more likely dependent upon a sharply focused retinal image than the ability to detect vernier misalignments. In particular, it is shown that a misalignment of the vernier targets is easily appreciated by a patient long after a comparable Snellen letter has been rendered unrecognizable due to blur.

To the extent that detecting misalignments of two stimuli during a hyperacuity test procedure is a simpler task than recognizing and identifying a figure so spatially complex as a Snellen letter, it can be concluded that measurements of a patient's hyperacuity will reveal more about the patient's visual function than the Snellen letter test, uncomplicated by considerations of the patient's ability or propensity to read and name letters. This desiderata of simplification is particularly pertinent for a patient population in which cerebrobascular disease and other health problems, comprising the "higher" mental functions, are frequently encountered.

The hyperacuity test for which applicant's instrument is especially designed is thus not limited by the enumerated drawbacks of the other test procedures briefly discussed above. First, no opening or "window" in the media opacity of a patient's eye is required to successfully conduct hyperacuity testing. Second, hyperacuity is so highly dependent upon retinal stimulus location that foveally and extra-foveally based responses are difficult to confuse when being compared; stimuli presented to a healthy fovea will unfailingly result in better performance than those presented to any extra-foveal location. The hyperacuities are also remarkably more robust to variations in stimulus luminants than those presented to any extra-foveal location.

The hyperacuities are also remarkably more robust to variations in stimulus luminants in contrast than are Snellen acuity and other indicies of visual resolution. These characteristics, when considered together with the resistance of the hyperacuities to stimulus blur, led applicants to recognize the potential clinical value of hyperacuity testing for evaluating retinal integrity behind ocular media opacities.

As further discussed in applicant's above-referenced publication, instrumentation was contemplated that only required two intense points of light whose relative positions could be controlled and ascertained with a high degree of precision. It was further suggested that the two points of light could be originated by use of an optically doubled laser beam for producing two-dot vernier stimulus. Applicant has incorporated these basic hyperacuity testing concepts into his instrument.

DISCLOSURE OF INVENTION

This invention provides a hyperacuity testing instrument, for evaluating visual function, that is non-complex, economical, exhibits a high degree of structural integrity and is easy to use.

The instrument is particularly adapted for use in developing countries where dense opacities of the ocular media are common and where surgical personnel and fiscal resources are limited. The instrument of this invention is not only capable of assessing vision through media with opacities of the lens (cataracts), but is also effective for assessing vision in respect to opacities of the cornea (leucomas) and vitreous (bleeds and membranes), resulting from keratomalacia, trachoma and other diseases more common in developing countries. As a result of pre-screening for potentially useful vision, a reduction, even in the range of 10% to 15% of non-productive surgery, would represent a substantial savings in terms of limited available ophthalmic manpower and resources and would have the beneficial effect of alleviating patient and family trauma.

The instrument comprises light producing means for producing at least two light beams, display means for receiving and visually displaying spots of the light beams for observation by a patient, first adjustment means for selectively varying the rotational positions of the spots relative to each other, and second adjustment means for selectively varying the separation gap between the spots.

As extensively discussed above, the instrument provides a clinician or surgeon with a valuable tool for evaluating the vision of a patient behind ocular opacities for the purpose of predicting the post-operative effects of a contemplated surgical procedure, i.e., to "penetrate" an opacity to assess visual function at the retinal-neural level.

BRIEF DESCRIPTION OF THE DRAWINGS

Other advantages and objects of this invention will become apparent from the following description and accompanying drawings wherein:

FIG. 1 is a frontal isometric view illustrating a hyperacuity testing instrument for evaluating visual function;

FIG. 3 schematically illustrates a bi-prism employed in the instrument utilized to split a single laser light beam B into two beams $B_1$ and $B_2$;

FIG. 10 is an isometric view illustrating a hyperacuity perimitry testing attachment for use with the testing instrument of FIGS. 1–6; and FIGS. 11 and 12 are enlarged sectional views, taken in the direction of arrows XI—XI and XII—XII in FIG. 10, respectively.

BEST MODE OF CARRYING OUT THE INVENTION

Definitions

The following definitions apply to various terms used herein and as they pertain to hyperacuity testing instrument 10:

Acuity: Clarity or clearness of vision.

Directional Bias: The arithmetic mean value of a patient's perceived vertical alignment (constant error) of spots $S_1$ and $S_2$.

Discrimination Threshold For Vernier Offset:

After determining the arithmetic mean of the offsets presented during a test procedure with the standard error of such data provides an indication of the estimated hyperacuity threshold and the reliability of the observer's judgements for the locus tested in the visual field.

Hyperacuity: A patient's ability to successfully perform any one of a group of visual tasks, each of which requires the discrimination of very fine differences in the spatial locations of two or more visual stimuli, such as spots or points of light.

Snellen's Chart: An eye chart, used to test visual acuity, imprinted with block letters (Snellen's test type) in gradually decreasing sizes, identified according to distances at which they are ordinarily visible.

Staircase Procedure: A two-stage series of test trials for determining an "offset threshold" for each gap setting. Spot $S_1$ is initially offset at a relatively large lateral distance from spot $S_2$ and on each trial the displacement is increased or decreased, depending on whether a patient's judgment (perception) was correct or incorrect. The offset is decreased by one step each time the patient makes a correct judgment, during an estimation phase. The first incorrect response terminates the estimation phase, whereafter two consecutive correct responses are required before the offset is further decreased. A single incorrect response causes the offset to increase by one step or level on the next trial. Other procedures such as the method of adjustment or limits may also be used.

Standard Error: The standard deviation divided by the square root of the number of trials.

Two-dot (spot) Vernier Task: The perceptional judgment of a patient as to whether spot $S_1$ is to the right, left or vertically aligned with spot $S_2$.

Vernier Acuity (Threshold Displacement): The threshold of perception of a break in continuity of a contour or of a border, e.g., a patient's threshold for detecting differences in the relative position of two points.

Visual Acuity: The relative ability of the visual organ to resolve detail that is usually expressed as the reciprocal of the minimum angular separation in minutes of arc of two lines just resolvable as separate and that forms in the average human eye an angle of one minute.

GENERAL DESCRIPTION

Figure 7:
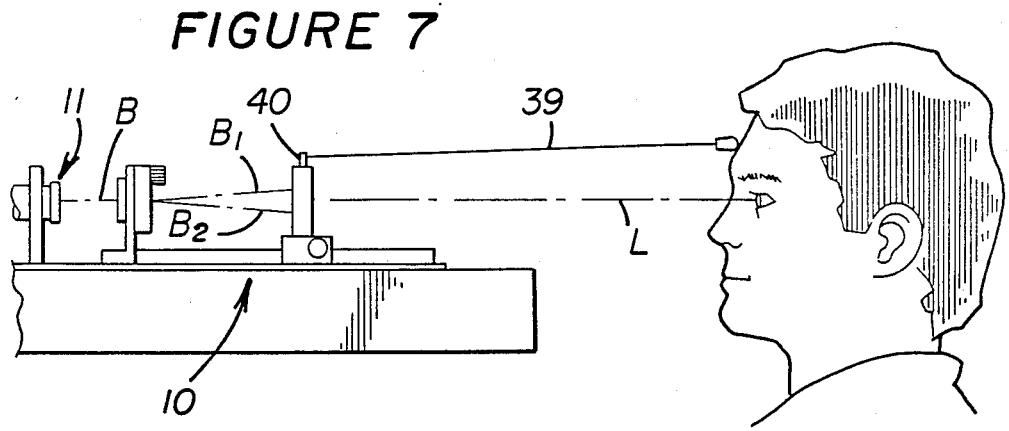
FIG. 7 illustrates use of the instrument by a patient for evaluating the patients vision.
Figure 2:
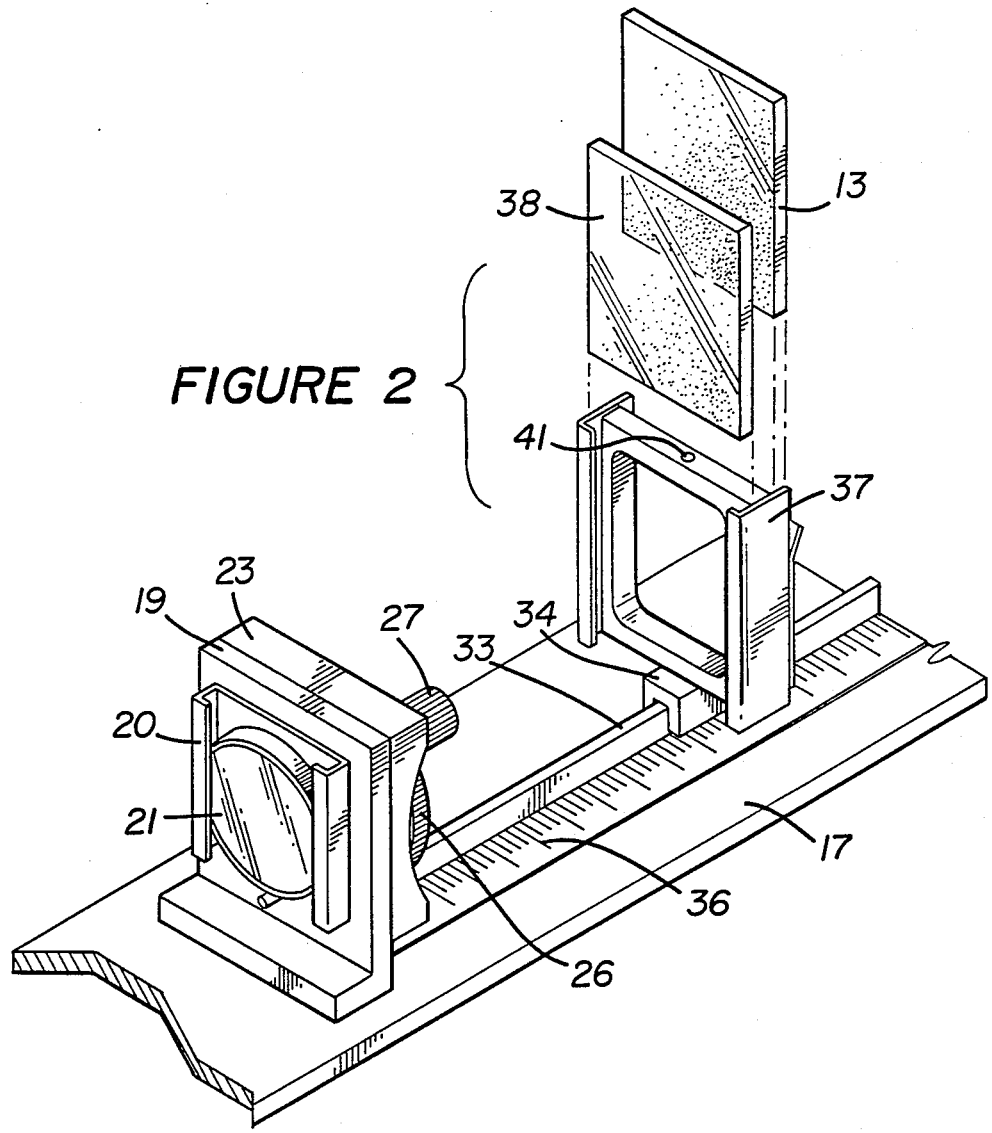
FIG. 2 is an enlarged partial view of the instrument, illustrating the backsides of a rotary stage and display screen assembly of the instrument.

FIGS. 1 and 2 illustrate a hyperacuity testing instrument 10 adapted to evaluate visual function in a manner hereinafter described. The instrument includes a laser head 11 for emitting a single laser beam B of light that is divided into two diverging beams $B_1$ and $B_2$ when it passes through a maddox bi-prism 12. The two laser beams impinge on a display screen 13 that visually displays the beams in the form of spots (dots or points) $S_1$ and $S_2$ for observation during the testing of a patient (FIG. 7).

As discussed above, the hyperacuity test procedure practiced by the instrument refers to a patient's ability to successfully discriminate very fine differences in the spatial locations of visual stimuli, shown in the form of light spots $S_1$ and $S_2$. In the instrument embodiment illustrated, the patient is tested to determine the patient's perception of: (1) the vertical alignment of the spots; and (2) the separation gap G between the spots.

The clinician or patient is enabled to selectively vary the rotational positions of the spots relative to each other ("vertical alignment") by manipulating a rotary stage device 14 to rotate and set bi-prism 12. The separation gap G between the spots is selectively varied by manipulating a linear stage device 15 to move and set display screen 13 linearly relative to the bi-prism.

The hyperacuity test procedure carried forth by use of the instrument is made possible due to the considerable data processing of the visual input which takes place in the patient's nervous system. Responses and data received from the patient differ from measurements of visual resolution, where a patient determines how many objects can be detected rather than where one object is located relative to another object or relative to an internal perception, e.g., the patient's sense of vertical, in the case of hyperacuity described.

In carrying forth the hyperacuity test procedure by use of instrument 10, the patient is simply asked to determine whether one spot $S_1$ or $S_2$ is to the right or left of the other spot or is requested to manipulate rotary stage device 14 to place the spots in vertical alignment. Obviously, the patient will fail at this task if the patient cannot discern the presence of the two spots, i.e., if the task becomes a judgement of resolution. In the presence of media opacities and without instruction, patients have been found to perform a surprisingly accurate center of gravity assessment, i.e., an ability to perceive and locate the center of each spot.

In the presence of star-burst or astigmatic distortions, performance is improved greatly by using a modest degree of low frequency spatial filtering, as described more fully hereinafter. Such filtering will function to remove the high spatial frequencies (essentially the borders of spots $S_1$ and $S_2$) and hence diminishes spurious resolution and other factors tending to confound judgments.

For these determinations, the vertical gap between the spots is varied. If the gap becomes too small, the response becomes a resolution task and performance suffers. If the gap is large enough to make a satisfactory judgment, hyperacuity is only slightly affected by media opacities. Obviously, if two points become separated by a large distance or gap, a patient's ability to align the spots will diminish. The shape of the resultant function and the necessary gap for best hyperacuity response is important in assessing the image degradation caused by the interposed ocular media opacity.

These measures are surprisingly insensitive to contrast or luminance variation once threshold detection of the two distributions is exceeded by a modest amount. If multiple images of each point are caused by the ocular media, e.g., as may be reported in posterior subcapsular cataract, the above-mentioned low frequency spatial filtering, a "white noise" background, and/or a small pinhole held close to the eye, will substantially improve measured hyperacuity performance.

When threshold vertical alignment of two points is measured (e.g., spots $S_1$ and $S_2$ in FIGS. 4-6), alignment bias and precision of measurement (hyperacuity threshold) can be differentiated. In the taking of predetermined number of measurements, bias will represent the mean alignment of these determinations. The presence of substantial bias (or constant error from the vertical) may indicate the presence of some degree or form of metamorphopsia. Precision of measurement, i.e., the fineness or consistency of judgments, is the measurement of hyperacuity. It can be estimated that from the variance of the number of measurements made. Determining the mean and variance for several different gap separations allows specification of a "hyperacuity gap function."

DETAILED DESCRIPTION

Returning to FIGS. 1 and 2, laser head 11 may comprise a 1 mw HeNe (helium-neon) laser head manufactured by C. W. Radiation, Inc., under Model No. 0EM1R. Although other types of laser heads can be used, this type is highly suitable for use in instrument 10 since it requires limited power (e.g., a standard 12 volt battery), directs substantially all of its energy in the desired direction, and the beam will pass through yellow lenses and even a modest (red-colored) bleed. A standard power supply 16 powers the laser head and may be of the type manufactured by C. W. Radiation, Inc. under Model No. LSS05.

Laser head 11 is mounted on a base 17 by a pair of longitudinally spaced and upstanding brackets 18. Rotary stage device 14 is mounted on an upstanding bracket 19 secured on base 17 and disposed forwardly of the laser head. As shown in FIG. 2, a holder 20 is secured on a backside of bracket 19 and mounts a standard neutral density filter thereon. The filter functions to reduce the brightness of red laser beam B.

Rotary stage device 14 includes a platform 23 suitably mounted on the frontal side of bracket 19. The rotary stage device may be of the type manufactured by Newport Research Corporation under Model No. RSX-1 and includes a dial 24 rotatably mounted on platform 23 by suitably arranged roller bearings (not shown). The dial has a 360° movable scale 25 imprinted thereon in two degree markings.

Dial 24 can be rotated a full 360° by finger pressure on a knurled edge 26 of the dial or by rotating a knob 27. The knob is connected by suitable gearing (not shown) to the dial for rotating the dial 60° upon each complete rotation of the knob. A set screw 28 is located on a side of platform 23 to lock the dial in position in a conventional manner. A scale 30 is imprinted on a fixed member 31 of the rotary staged device with the scale giving vernier readings of 12 minutes of arc on either side of midpoint "0".

Twelve minutes of arc dial setting is sufficient as expressed as follows (FIG. 8):

r = the gap size expressed as visual angle in minutes of arc.
x = the displacement from vertical expressed as visual angle in seconds of arc.
$\theta$ = the dial setting in minutes of arc.
x = r tan $\theta$ where $\theta$ is small and is expressed in radians. Then, the following approximation can be used:
x ≃ r$\theta$ and the change in x for a change in $\theta$ is:
$\Delta x \simeq \Delta \theta \Delta \theta$ is 12 min. of arc (the minimum dial calibration or 0.0035 in radians.

For a gap of 32 min. of arc, convert to secs. of arc:
32 min arc → 1920 secs. of arc.
$\Delta x$ = 1920 × 0.0035 = 6.7 secs. of arc.
Similarly:

| GAP | DISPLACEMENT |
| --- | --- |
| 2 min of arc | 0.4 secs. of arc |
| 8 min of arc | 1.6 secs. of arc |
| 32 min of arc | 6.7 secs. of arc |
| 128 min of arc | 26.9 secs. of arc |
| 512 min of arc | 107.5 secs. of arc |

While there is increasing minimum displacement size accuracy for larger gaps, hyperacuity falls off at larger gaps as well.

Figure 4:
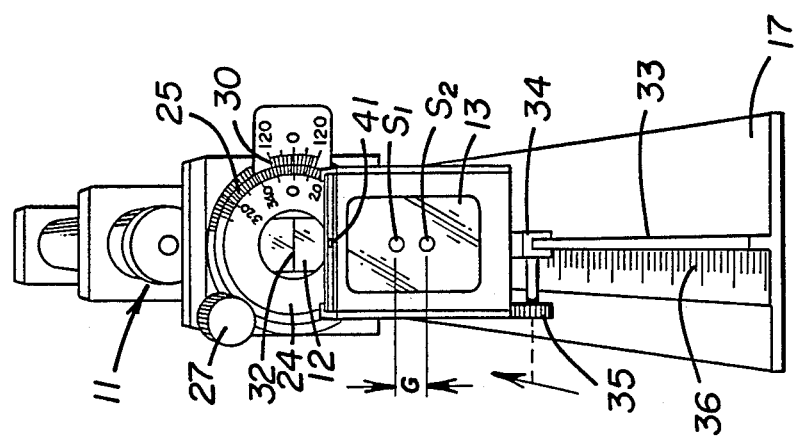

As shown in FIGS. 1, 3, and 4, bi-prism 12 may constitute a standard Maddox bi-prism mounted centrally in dial 24. In the "0" setting of the dial, the apex or frontal edge 32 of the bi-prism will be disposed horizontally (FIGS. 1 and 4) for true vertical alignment of spots $S_1$ and $S_2$. As shown in FIG. 3, an apical angle A of the bi-prism will depend on the construction and arrangement of a particular instrument 10. The greater the angle, of course, the smaller the angle of divergence D between split beams $B_1$ and $B_2$. In one experimental model, such apical angle constituted 170° with successful results.

Figure 6:
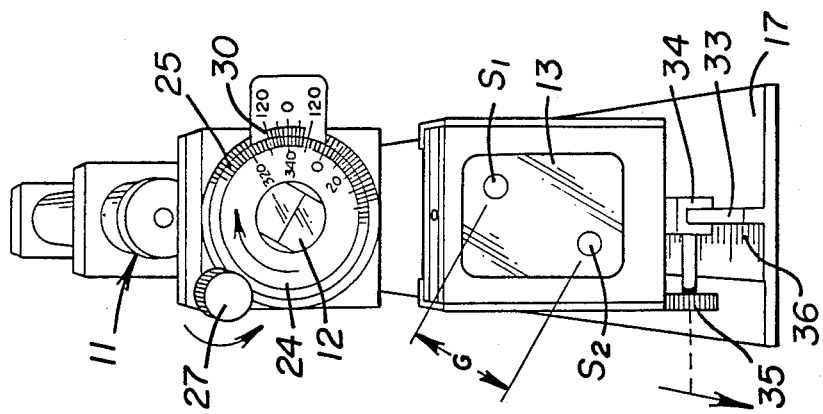
FIGS. 4–6 are frontal views illustrating the instrument in various modes of operation.
Figure 5:
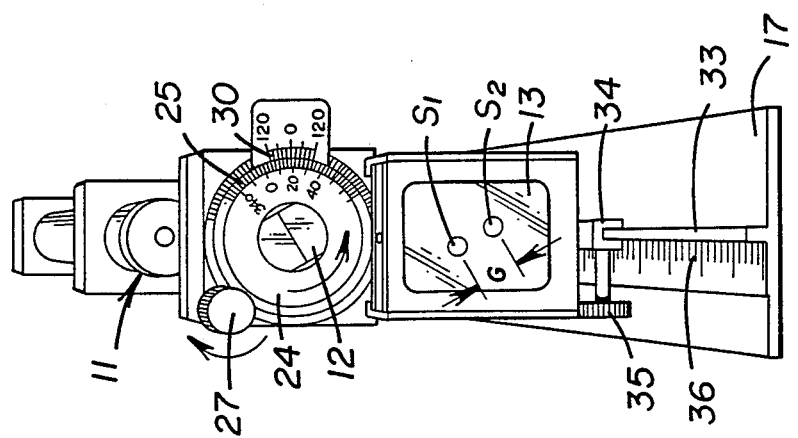

Referring to FIGS. 1 and 2, linear stage device 15 comprises a longitudinally disposed guide bar 33 secured on base 17 to extend in parallel relationship relative to the longitudinal axis of the instrument and laser beam B. An inverted channel 34 is slidably mounted on the rail to provide a track system for selectively adjusting the separation gap G between spots $S_1$ and $S_2$ on display screen 13 when the display screen is moved linearly relative to rotary staged device 14 (FIGS. 4-6). A set screw 35 is threadably mounted on a side of the channel to have its distal end engage guide bar 33 in bearing contact to lock the linear stage device in a fixed position. A linear scale 36 is secured on base 17 in alignment with guide bar 33 to set the linear distance between bi-prism 12 and display screen 13, which distance can be correlated into the distance between the centers of spots $S_1$ and $S_2$ for any selected linear setting of the screen.

As shown in FIG. 2, display screen 13 is mounted in an upstanding bracket 37 secured on channel 34. The display screen is preferably composed of a standard translucent ground glass material having the proper imaging qualities to clearly display laser beam spots $S_1$ and $S_2$ thereon. In certain applications of this invention, it has proven desirable to further mount a ground glass window 38 on a rearward side of display screen 13 to render laser beams $B_1$ and $B_2$ less directional and to allow a patient with a dense opacity to be more easily aligned with the instrument. In one experimental model of the instrument, display screen 13 and window 38 were separated by a distance closely approximating 0.80 cm.

EXAMPLE-TEST PROCEDURE

As shown in FIG. 7, a patient is positioned on a frontal side of instrument 10 with the patient's eye level L being disposed in substantial alignment with display screen 13. A measuring tape 39 has a distal end adapted to be releasably attached on bracket 37 by a pin 40 (FIGS. 2 and 7), inserted in an accommodating hole 41. The pre-adjusted and locked position of display screen 13, relative to bi-prism 12, and the linear distance between the display screen and the patient's eye can be located and recorded by a clinician by reference to linear scale 36 and tape measure 39, respectively.

The clinician or patient can rotate bi-prism 12 by manipulation of knurled edge 26 of dial 24 or knob 27 to achieve the patient's perceived vertical alignment of spots $S_1$ and $S_2$ for a given number of trials for each gap setting (present linear adjustment of screen 13 relative to bi-prism 12). The clinician will offset the bi-prism a predetermined amount after recording each threshold measurement. This is a method of adjustment technique.

Alternatively, a staircase technique can be used to estimate the limits of a patient's ability to detect the misalignment of the two spots when measuring vernier acuity. Otherwise stated, the relative lateral displacement of the spots is increased or decreased in a stepwise manner and the results recorded. The range of vernier offsets to be presented is adjusted, according to the patients responses so as to span the range from offsets that are below the patient's discrimination threshold to others that are easily appreciated and perceived. A configuration wherein the two spots are exactly aligned vertically is also included in the test procedure and is useful in the statistical analysis of responses.

Normally, the staircase technique requires only about 25 stimulus presentations (total time, 10 to 20 min.) per threshold estimate. Testing normally begins with a large, easily appreciated vernier offset in a "search" phase of testing, during which each correct response results in a decrease of the offset by one level and each incorrect response results in an equivalent increase. The "search" phase, designed to rapidly converge to offsets near threshold, continues until two incorrect responses have been recorded. From this point on (i.e., in the "test phase"), two consecutively correct responses are required at each offset before the offset is decreased, while a single incorrect response will increase the offset value by one level. Data collection is terminated after nine reversals in the direction (i.e., increasing or decreasing offset) of the staircase.

Figure 8:
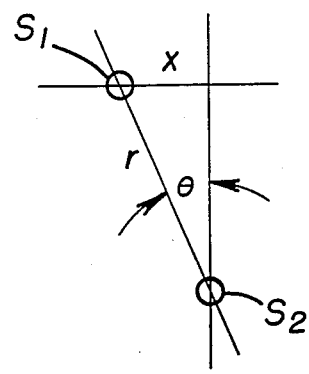
FIG. 8 illustrates a dial setting and gap size, used for explanation purposes hereinafter.
Figure 9:
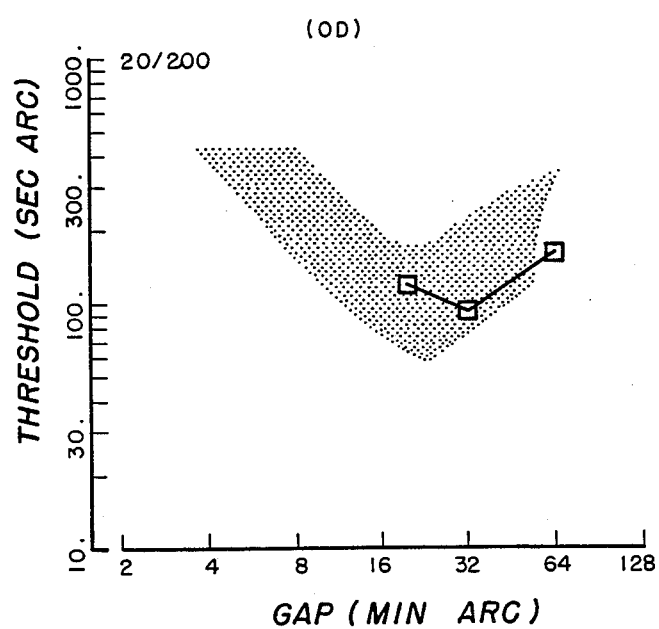
FIG. 9 diagramatically illustrates an example of a gap function obtained by use of the instrument.

FIG. 8 graphically illustrates a gap function determined from the following data, obtained with instrument 12. The test procedure was conducted on a patient having corneal edema and Snellen acuity of 20-200 (or decimal acuity of 0.10).

The numbered columns depict the following: (1) Setting of gaps (min. arc); (2) The linear distance between screen 13 and the patient's eye as measured by tape measure 39 (cm.); (3) The liner distance between bi-prism 12 and screen 13 as measured on scale 36 (cm.); (4) Separation gap G (mm); and (5) Mean of five settings of dial 24 (min. arc); and (6) Thresholds—standard deviations (sec. arc):

| TRIAL | (1) | (2) | (3) | (4) | (5) | (6) |
|---|---|---|---|---|---|---|
| 1 | 20 | 95.5 | 4.5 | 5.5 | 49.3 | 120.24 |
| 2 | 32 | 93 | 7.2 | 8.6 | −28.6 | 93.29 |
| 3 | 64 | 86.5 | 13.6 | 16.1 | 148.0 | 160.02 |

The mean of 5 settings was plotted for each of the three gaps tested (open squares). The stipled area illustrates the range values obtained with a more sophisticated laboratory version of instrument 10 on otherwise-normal cataract patients with comparable acuities.

A method of adjustment technique was used. It should be noted that the "optimum gap" for patients with corneal opacities is typically somewhat greater than for patients with lenticular opacities and comparable visual acuities.

As discussed above, the essence of measuring vernier acuity lies in simply requiring the patient to indicate the patient's perception of whether spot $S_1$ lies to the right or to the left of spot $S_2$. It makes little difference whether the two spots are sharply defined or are perceived merely as diffuse blobs of light. Each spot will have a diameter approximately within the range of from 1.0 to 2.0 min. arc with the centers of the spots being separated by gap G. The luminance of the spots are preferably within the range of from 100 to 550 cd/m$^2$.

It has been found desirable to maintain the room in which the patient is being tested with dim illumination so as to provide the maximum possible stimulus contrast. If the patient exhibits a dense cataract, performance is oftentimes improved by enhancing the illuminance of screen 13, that is, removing neutral density filter 21.

In the hyperacuity "gap test", the clinician measures the effect that varying the vertical gap G (FIG. 4) between spots $S_1$ and $S_2$ has upon a patient's ability to detect horizontal offsets of one dot relative to the other. Testing is performed monocularly with the eye demonstrating better Snellen acuity (standard eye chart) tested first, for purposes of training the observer. This test is begun by using a gap size G which is expected to be optimal for the patient.

This initial procedure serves to familiarize the patient with the task involved and provides baseline data against which results from the poor eye can be compared. Testing proceeds by using gap sizes differing by a factor of 2 (e.g., 1, 2, 4, 8 . . . min. arc) until a complete threshold versus gap function and an optimum gap size have been obtained. Allowing for repeated measurements with some gap sizes, will normally require lesser testing time for the method of adjustment technique than with the staircase method. Shorter test series can be conducted on elderly or infirm patients. Obviously, reducing trials decreases reliability.

FIGS. 10-12 illustrate a hyperacuity perimetry testing attachment for instrument 10 wherein an additional fixation light is attached to brakcet 37 at desired distances to allow assessment of different locations in the visual field. The attachment comprises an arm 42, shown in the form of an angle, having a linear scale 43 thereon and its proximal end attached to a block 44 secured beneath the bracket. A second, identical block is secured beneath the opposite side of the bracket to adapt arm 42 for attachment thereto.

As shown in FIG. 11, a clamping block 46 and screw 47 function to releasably clamp the arm to block 44 and bracket 37. A bracket 48 is adjustably mounted for selected longitudinal movement on arm 42 and is adapted to be clamped thereto by a standard spring clip 49. A green light emitting diode (LED) is attached forwardly on the bracket for observation by a patient to measure the patient's spatial discrimination capability.

In particular, the patient will fixate on the green light so that the hyperacuity display (spots $S_1$, $S_2$) are in the patient's peripheral field. A two alternative forced-choice test is again used to determine the patient's hyperacuity threshold. The light can be moved linearly to several locations on arm 42 during the test to obtain a meridian across the patient's field of vision. Thus, a perimetric profile of the patient's spatial discrimination capability can be obtained.

We claim:

1. A hyperacuity testing instrument for evaluating visual function comprising
   light producing means for producing at least two beams of coherent light,
   display means positioned for receiving and visually displaying spots of said beams for observation by a patient within a patient's field of vision to determine the alignment and separation gap between said spots,
   first adjustment means for selectively moving said spots simultaneously to vary the rotational positions and alignment of said spots relative to each other, and
   second adjustment means for selectively varying the separation gap between said spots.

2. The hyperacuity testing instrument of claim 1 wherein said light producing means comprises a laser for emitting a single beam of light and a bi-prism longitudinally spaced forwardly of said laser and in alignment with said beam to split said beam into two beams diverging relative to each other forwardly of said bi-prism.

3. The hyperacuity testing instrument of claim 2 wherein said first adjustment means comprises a rotary stage device having a dial rotatably mounted thereon and means for measuring the rotated position of said dial and the rotational positions of said spots relative to each other, said bi-prism mounted centrally within said dial.

4. The hyperacuity testing instrument of claim 3 wherein said second adjustment means comprises track means for moving said display means longitudinally in linear alignment with said bi-prism and means on said instrument for measuring the linear distance between said display means and said bi-prism.

5. The hyperacuity testing instrument of claim 4 wherein said display means comprises at least one ground glass member mounted in an upstanding bracket and wherein said track means comprises an inverted channel having said bracket secured thereon, and a longitudinally disposed guide bar having said channel slidably mounted thereon.

6. The hyperacuity testing instrument of claim 5 further comprising means for locking said channel to said guide bar at a selected linear position thereon.

7. The hyperacuity testing instrument of claim 5 further comprising a second ground glass member mounted on a backside of said bracket and longitudinally separated slightly from said first mentioned member providing means for scattering light and for functioning as a low pass spatial filter.

8. The hyperacuity testing instrument of claim 2 further comprising a neutral density filter means longitudinally positioned between said laser and said bi-prism for reducing the brightness of said beam.

9. The hyperacuity testing instrument of claim 1 further comprising means for locating and measuring the distance between said display means and an eye of a patient positioned forwardly of said display means.

10. The hyperacuity testing instrument of claim 1 further comprising hyperacuity perimetry testing means extending transversely from said display means for measuring a patient's spatial discrimination capability.

11. The hyperacuity testing instrument of claim 10 wherein said hyperacuity perimetry testing means comprises an arm attached to said display means, a linear scale on said arm and light emitting means adjustably mounted on said arm for movement therealong.

12. A mobile hyperacuity testing instrument for evaluating visual function comprising
    a base,
    a laser means secured on said base for emitting a single beam of light in the direction of a longitudinal axis thereof,
    a rotary stage device mounted forwardly of said laser means, said rotary stage device comprising
    an upstanding bracket secured on said base,
    a dial rotatably mounted on a frontal side of said bracket,
    bi-prism means mounted centrally on said dial for splitting said single beam into a pair of beams diverging relative to each other, forwardly of said bi-prism, and
    first means for measuring the relative rotative positions of said beams in minutes and seconds of arc,
    display screen means mounted on said base, forwardly and in longitudinal alignment with said bi-prism, for displaying spots of said beams thereon,
    adjustment means for moving said display screen means longitudinally relative to said bi-prism for selectively varying the separation gap between said spots, and
    second means for measuring the separation gap between said spots.

13. The mobile hyperacuity testing instrument of claim 12 wherein said adjustment means comprises track means for moving said display screen means longitudinally in linear alignment with said bi-prism and wherein said second means comprises a linear scale on said base for measuring the linear distance between said display screen means and said bi-prism means.

14. The mobile hyperacuity testing instrument of claim 13 wherein said display screen means comprises at least one ground glass member mounted in an upstanding second bracket and wherein said track means comprises an inverted channel having said second bracket secured thereon, and a longitudinally disposed guide bar secured on said base and having said channel slidably mounted thereon.

15. The mobile hyperacuity testing instrument of claim 14 further comprising means for locking said channel to said guide bar at a selected linear position thereon.

16. The mobile hyperacuity testing instrument of claim 14 further comprising a second ground glass member mounted on a backside of said second bracket and longitudinally separated slightly from said first-mentioned member.

17. The mobile hyperacuity testing instrument of claim 12 further comprising neutral density filter means longitudinally positioned between said laser means and said bi-prism means for reducing the brightness of said beam.

18. The mobile hyperacuity testing instrument of claim 12 further comprising means for locating and measuring the distance between said display screen means and an eye of a patient positioned forwardly of said display screen means.

19. The mobile hyperacuity testing instrument of claim 12 further comprising hyperacuity perimetry testing means extending transversely from said display screen means for measuring a patient's spatial discrimination capability.

20. The mobile hyperacuity testing instrument of claim 19 wherein said hyperacuity perimetry testing means comprises an arm attached to said display screen means, a linear scale on said arm and light emitting means adjustably mounted on said arm for movement therealong.

* * * * *